United States Patent
Sim et al.

(10) Patent No.: US 11,533,394 B2
(45) Date of Patent: Dec. 20, 2022

(54) ELECTRONIC DEVICE COMPRISING EARPHONE JACK INTEGRALLY FORMED WITH GAS SENSOR

(71) Applicant: Samsung Electronics Co., Ltd., Gyeonggi-do (KR)

(72) Inventors: Bo Kyung Sim, Gyeonggi-do (KR); Jeong Gyu Jo, Gyeonggi-do (KR); Seung Goo Kang, Gyeonggi-do (KR); Ik Joo Byun, Gyeonggi-do (KR); Hee Kang Yun, Gyeonggi-do (KR); Jin Ho Lim, Gyeonggi-do (KR); Dong Il Son, Gyeonggi-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 16/763,297

(22) PCT Filed: Oct. 25, 2018

(86) PCT No.: PCT/KR2018/012735
§ 371 (c)(1),
(2) Date: May 12, 2020

(87) PCT Pub. No.: WO2019/124716
PCT Pub. Date: Jun. 27, 2019

(65) Prior Publication Data
US 2020/0322470 A1  Oct. 8, 2020

(30) Foreign Application Priority Data

Dec. 22, 2017 (KR) .................. 10-2017-0178538

(51) Int. Cl.
*H04M 1/21* (2006.01)
*G01N 33/00* (2006.01)
*H04M 1/725* (2021.01)

(52) U.S. Cl.
CPC .......... *H04M 1/21* (2013.01); *G01N 33/0036* (2013.01); *H04M 1/725* (2013.01)

(58) Field of Classification Search
CPC ...................................................... H04M 1/21
See application file for complete search history.

(56) References Cited

U.S. PATENT DOCUMENTS

2004/0046008 A1   3/2004  Raghavan et al.
2007/0284229 A1*  12/2007  Chen .................. H01R 13/5213
                                                        200/43.18

(Continued)

FOREIGN PATENT DOCUMENTS

EP        3240272 A1    11/2017
KR     10-0690638 B1     2/2007

(Continued)

OTHER PUBLICATIONS

European Search Report dated Oct. 9, 2020.

*Primary Examiner* — Hsinchun Liao
(74) *Attorney, Agent, or Firm* — Cha & Reiter, LLC

(57) ABSTRACT

An electronic device according to various embodiments of the present invention may comprise: a housing including a hole formed therethrough; an earphone jack built in the housing such that an earphone plug is received therein through the hole; a gas sensor integrally formed with the earphone jack; a memory positioned inside the housing; and a processor positioned inside the housing and electrically connected with the earphone jack, the gas sensor, and the memory, wherein the memory stores instructions by which, when executed, the processor: controls the gas sensor to obtain data related to a specific component of the outside air; and causes the gas sensor to calculate a cleanliness level of the outside air on the basis of at least one of data obtained before a predetermined measurement disturbance element is (Continued)

generated and data obtained after the measurement disturbance element is removed. Other various embodiments are also possible.

10 Claims, 14 Drawing Sheets

(56) References Cited

U.S. PATENT DOCUMENTS

| | | |
|---|---|---|
| 2010/0216526 A1 | 8/2010 | Chen et al. |
| 2014/0193018 A1 | 7/2014 | Lim et al. |
| 2014/0262847 A1* | 9/2014 | Yang .................. F16M 13/022 |
| | | 206/37 |
| 2014/0349707 A1 | 11/2014 | Bang |
| 2017/0318135 A1 | 11/2017 | Han et al. |
| 2019/0170716 A1 | 6/2019 | Sim et al. |

FOREIGN PATENT DOCUMENTS

| | | |
|---|---|---|
| KR | 10-1246726 B1 | 3/2013 |
| KR | 10-1260962 B1 | 5/2013 |
| KR | 10-2014-0089768 A | 7/2014 |
| KR | 10-2017-0123206 A | 11/2017 |
| KR | 10-2019-0066474 A | 6/2019 |

* cited by examiner

ELECTRONIC DEVICE COMPRISING EARPHONE JACK INTEGRALLY FORMED WITH GAS SENSOR

CROSS REFERENCE TO RELATED APPLICATIONS

This application is a National Phase Entry of PCT International Application No. PCT/KR2018/012735, which was filed on Oct. 25, 2018, and claims a priority to Korean Patent Application No. 10-2017-0178538, which was filed on Dec. 22, 2017, the contents of which are incorporated herein by reference.

TECHNICAL FIELD

Various embodiments of the disclosure relate to an electronic device having an earphone jack integrally formed with a gas sensor configured to analyze components of outside air.

BACKGROUND ART

Measurements of air cleanliness levels are performed in a limited number of places designated by a specific institution. However, recently, the importance of air cleanliness levels has been on the rise, and thus, a gas sensor may be mounted to mobile electronic devices (e.g., smartphones).

DISCLOSURE OF INVENTION

Technical Problem

In the case where a gas sensor is mounted to an electronic device, a hole for direct connection with the outside is required. However, the recent design of a mobile electronic device has a tendency to reduce holes formed on the outside thereof.

Various embodiments of the disclosure propose a structure in which a gas sensor is integrally formed with an earphone jack in an electronic device. In addition, various embodiments propose an electronic device configured to perform functions, based on information obtained through a gas sensor.

Solution to Problem

An electronic device according to various embodiments of the disclosure may include: a housing having a hole formed therethrough; an earphone jack built in the housing so as to receive an earphone plug therein through the hole; a gas sensor integrally formed with the earphone jack; a memory positioned inside the housing; and a processor positioned inside the housing and electrically connected to the earphone jack, the gas sensor, and the memory, wherein the memory may store instructions that cause, when executed, the processor to: control the gas sensor so as to obtain data related to a specific component of outside air; and calculate a cleanliness level of the outside air, based on at least one piece of data obtained by the gas sensor before a predetermined measurement disturbance element is generated or data obtained by the gas sensor after the measurement disturbance element is removed.

An electronic device according to various embodiments of the disclosure may include: a housing having a first hole and a second hole formed therethrough; an earphone jack built in the housing so as to receive an earphone plug therein through the first hole; a gas sensor integrally formed with the earphone jack; a microphone built in the housing so as to lead to the outside through the second hole; a proximity sensor positioned inside the housing; a wireless communication module positioned inside the housing; a memory positioned inside the housing; and a processor positioned inside the housing and electrically connected with the earphone jack, the gas sensor, the microphone, the proximity sensor, the wireless communication module, and the memory, wherein the first hole and the second hole may be formed on one side surface of the housing, and wherein the memory may store instructions that cause, when executed, the processor to: recognize an operation of initiating a user's proximity call, based at least on data obtained from the proximity sensor, while communicating with an external device through the wireless communication module; and measure a user's health condition, based at least on data obtained by the gas sensor after recognizing the operation of initiating the proximity call.

A method for operating an electronic device according to various embodiments of the disclosure may include: obtaining data related to a specific component of outside air by a gas sensor of the electronic device; recognizing the occurrence of a predetermined measurement disturbance element by a processor of the electronic device; and calculating a cleanliness level of the outside air by the processor, based on at least one piece of data obtained by the gas sensor before the measurement disturbance element is generated or data obtained by the gas sensor after the measurement disturbance element is removed, wherein the measurement disturbance element may be an operation of inserting an earphone plug into an earphone jack of the electronic device or an operation of initiating a user's proximity call.

Advantageous Effects of Invention

Various embodiments of the disclosure are able to provide a mobile electronic device capable of measuring gas through an existing hole that is used for other purposes (for example, reception of an earphone plug) without providing a separate hole for a gas sensor. In addition, various embodiments of the disclosure are able to provide an electronic device configured to perform functions, based on the information obtained through a gas sensor.

MODE FOR THE INVENTION

Figure 1:
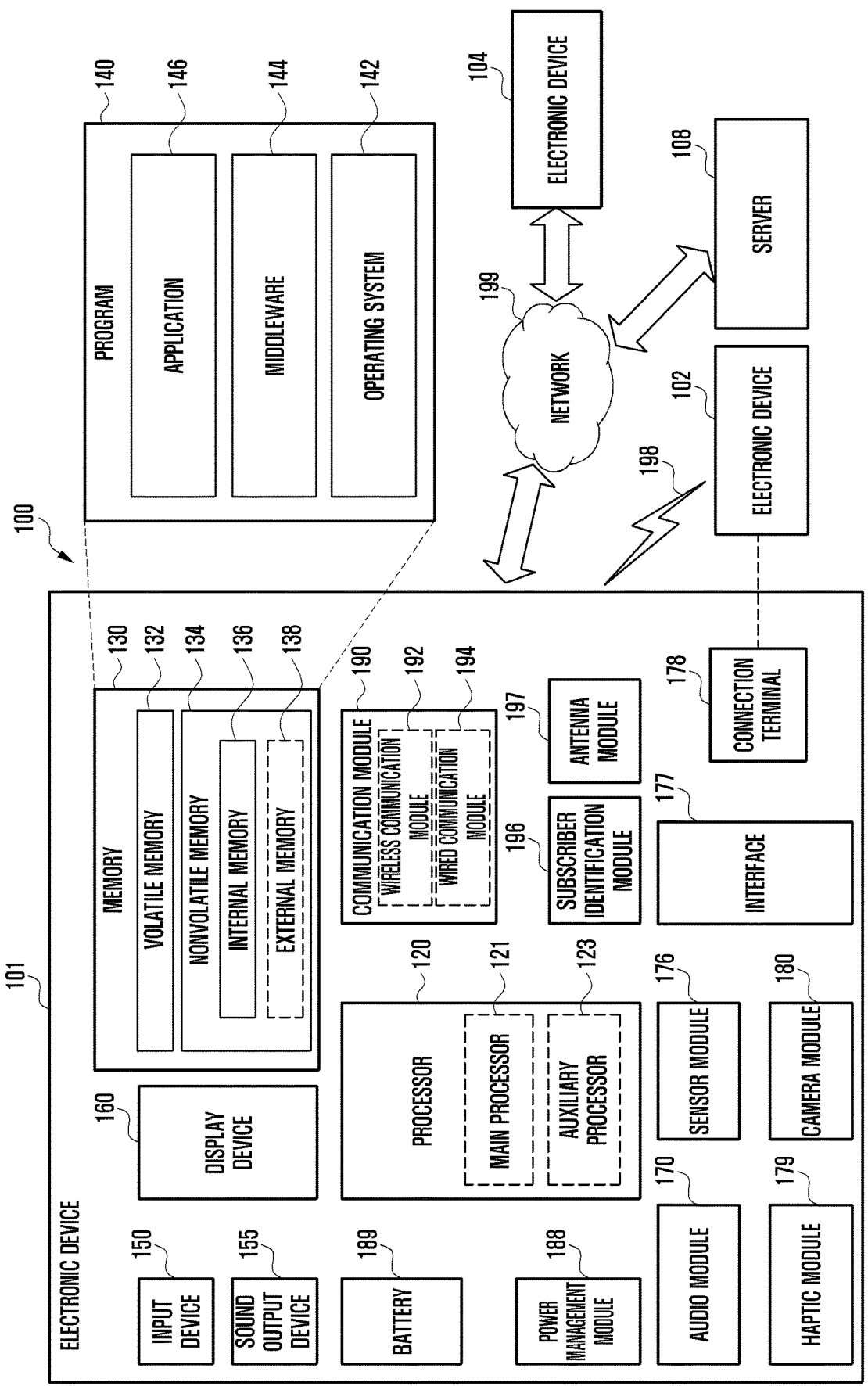
FIG. 1 illustrates an electronic device in a network environment according to various embodiments.

FIG. 1 is a block diagram illustrating an electronic device 101 in a network environment 100 according to various embodiments. Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (SIM) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to one embodiment, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by other component (e.g., the processor 120) of the electronic device 101, from the outside (e.g., a user) of the electronic device 101. The input device 150 may include, for example, a microphone, a mouse, a keyboard, or a digital pen (e.g., a stylus pen).

The sound output device 155 may output sound signals to the outside of the electronic device 101. The sound output device 155 may include, for example, a speaker or a receiver. The speaker may be used for general purposes, such as playing multimedia or playing record, and the receiver may be used for an incoming calls. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or a headphone of an external electronic device (e.g., an electronic device 102) directly (e.g., wiredly) or wirelessly coupled with the electronic device 101.

The sensor module 176 may detect the operation state (e.g., power or temperature) of the electronic device 101 or the external environmental state (e.g., the user state), and may generate an electrical signal or a data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, a gas sensor (e.g., an electronic nose sensor), or an illuminance sensor. In a certain embodiment, a plurality of sensors (e.g., a temperature sensor, a humidity sensor, and a gas sensor) may be integrated into one sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to one embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device) of the electronic device 101. According to an embodiment, the antenna module 197 may include an antenna including a radiating element composed of a conductive material or a conductive pattern formed in or on a substrate (e.g., PCB). According to an embodiment, the antenna module 197 may include a plurality of antennas. In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 and 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

Figure 2:
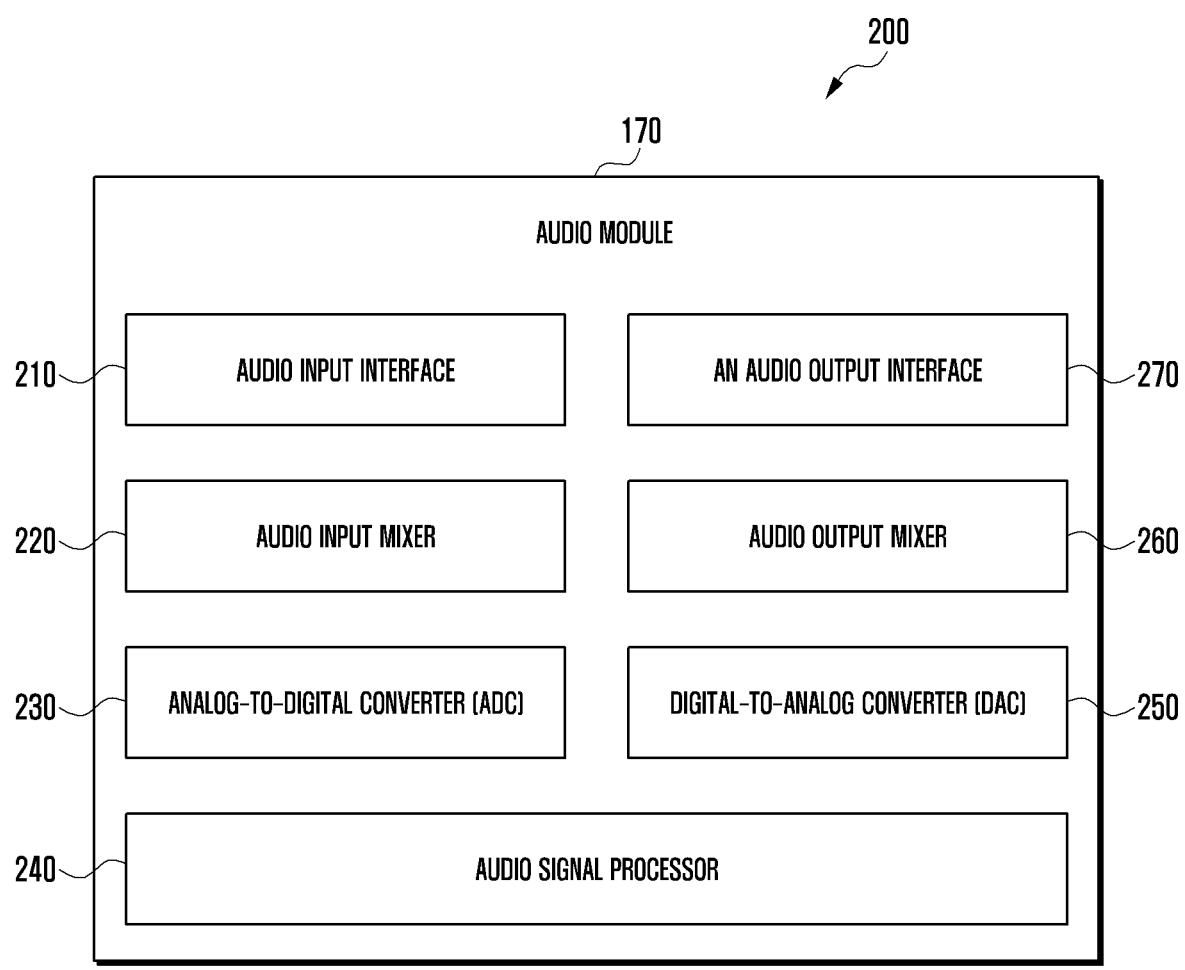
FIG. 2 is a block diagram of an audio module according to various embodiments.

FIG. 2 is a block diagram 200 illustrating the audio module 170 according to various embodiments. Referring to FIG. 2, the audio module 170 may include, for example, an audio input interface 210, an audio input mixer 220, an analog-to-digital converter (ADC) 230, an audio signal processor 240, a digital-to-analog converter (DAC) 250, an audio output mixer 260, or an audio output interface 270.

The audio input interface 210 may receive an audio signal corresponding to a sound obtained from the outside of the electronic device 101 via a microphone (e.g., a dynamic microphone, a condenser microphone, or a piezo microphone) that is configured as part of the input device 150 or separately from the electronic device 101. For example, if an audio signal is obtained from the external electronic device 102 (e.g., a headset or a microphone), the audio input interface 210 may be connected with the external electronic device 102 directly via the connecting terminal 178, or wirelessly (e.g., Bluetooth™ communication) via the wireless communication module 192 to receive the audio signal. According to an embodiment, the audio input interface 210 may receive a control signal (e.g., a volume adjustment signal received via an input button) related to the audio signal obtained from the external electronic device 102. The audio input interface 210 may include a plurality of audio input channels and may receive a different audio signal via a corresponding one of the plurality of audio input channels, respectively. According to an embodiment, additionally or alternatively, the audio input interface 210 may receive an audio signal from another component (e.g., the processor 120 or the memory 130) of the electronic device 101.

The audio input mixer 220 may synthesize a plurality of inputted audio signals into at least one audio signal. For example, according to an embodiment, the audio input mixer 220 may synthesize a plurality of analog audio signals inputted via the audio input interface 210 into at least one analog audio signal.

The ADC 230 may convert an analog audio signal into a digital audio signal. For example, according to an embodiment, the ADC 230 may convert an analog audio signal received via the audio input interface 210 or, additionally or alternatively, an analog audio signal synthesized via the audio input mixer 220 into a digital audio signal.

The audio signal processor 240 may perform various processing on a digital audio signal received via the ADC 230 or a digital audio signal received from another component of the electronic device 101. For example, according to an embodiment, the audio signal processor 240 may perform changing a sampling rate, applying one or more filters, interpolation processing, amplifying or attenuating a whole or partial frequency bandwidth, noise processing (e.g., attenuating noise or echoes), changing channels (e.g., switching between mono and stereo), mixing, or extracting a specified signal for one or more digital audio signals. According to an embodiment, one or more functions of the audio signal processor 240 may be implemented in the form of an equalizer.

The DAC 250 may convert a digital audio signal into an analog audio signal. For example, according to an embodiment, the DAC 250 may convert a digital audio signal processed by the audio signal processor 240 or a digital audio signal obtained from another component (e.g., the processor (120) or the memory (130)) of the electronic device 101 into an analog audio signal.

The audio output mixer 260 may synthesize a plurality of audio signals, which are to be outputted, into at least one audio signal. For example, according to an embodiment, the audio output mixer 260 may synthesize an analog audio signal converted by the DAC 250 and another analog audio signal (e.g., an analog audio signal received via the audio input interface 210) into at least one analog audio signal.

The audio output interface 270 may output an analog audio signal converted by the DAC 250 or, additionally or alternatively, an analog audio signal synthesized by the audio output mixer 260 to the outside of the electronic device 101 via the sound output device 155. The sound output device 155 may include, for example, a speaker, such as a dynamic driver or a balanced armature driver, or a receiver. According to an embodiment, the sound output device 155 may include a plurality of speakers. In such a case, the audio output interface 270 may output audio signals having a plurality of different channels (e.g., stereo channels or 5.1 channels) via at least some of the plurality of speakers. According to an embodiment, the audio output interface 270 may be connected with the external electronic device 102 (e.g., an external speaker or a headset) directly via the connecting terminal 178 or wirelessly via the wireless communication module 192 to output an audio signal.

According to an embodiment, the audio module 170 may generate, without separately including the audio input mixer 220 or the audio output mixer 260, at least one digital audio signal by synthesizing a plurality of digital audio signals using at least one function of the audio signal processor 240.

According to an embodiment, the audio module 170 may include an audio amplifier (not shown) (e.g., a speaker amplifying circuit) that is capable of amplifying an analog audio signal inputted via the audio input interface 210 or an audio signal that is to be outputted via the audio output interface 270. According to an embodiment, the audio amplifier may be configured as a module separate from the audio module 170.

Figure 3:
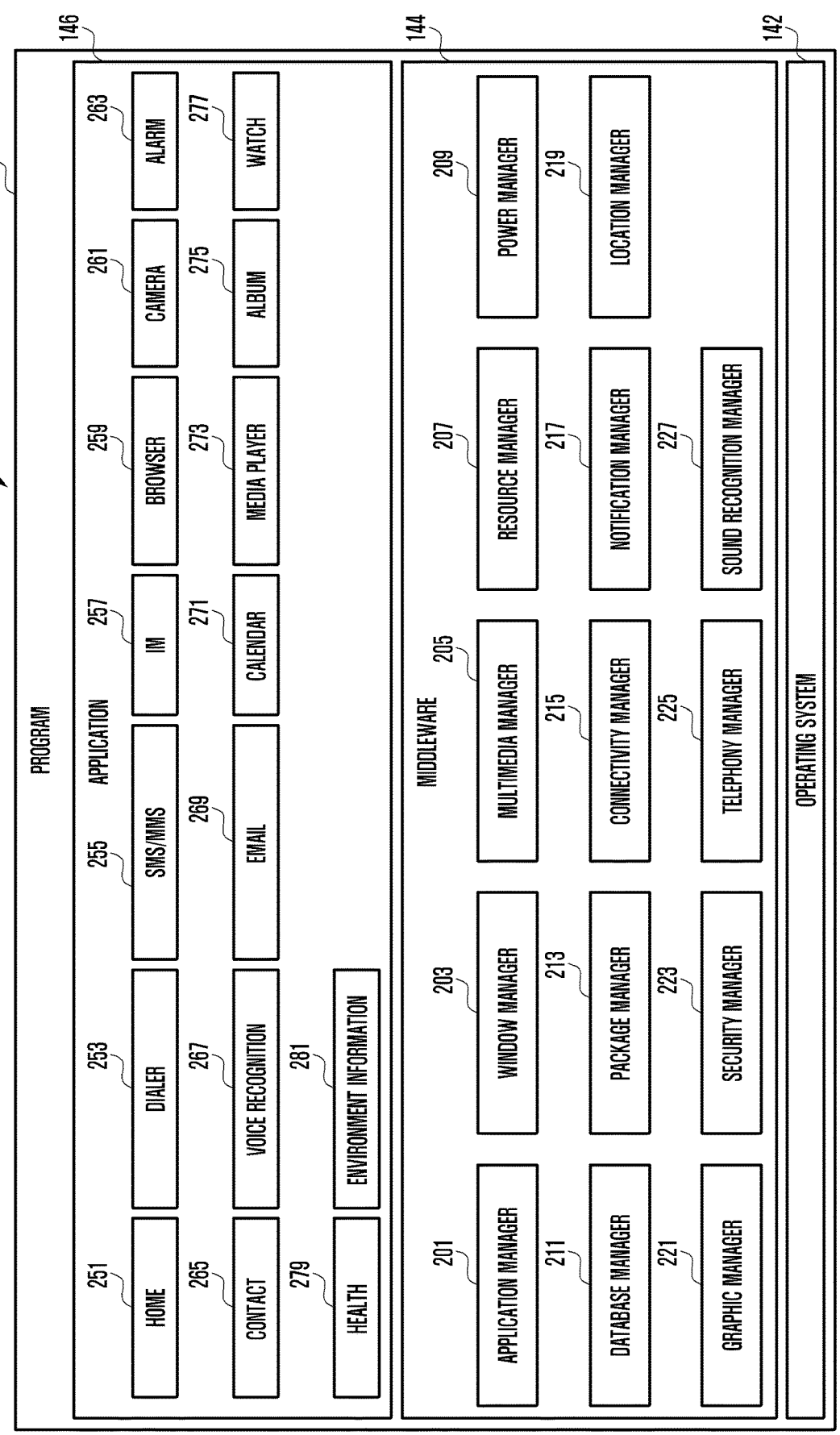
FIG. 3 is a block diagram of a program according to various embodiments.

FIG. 3 is a block diagram 300 illustrating the program 140 according to various embodiments. According to an embodiment, the program 140 may include an operating system (OS) 142 to control one or more resources of the electronic device 101, middleware 144, or an application 146 executable in the OS 142. The OS 142 may include, for example, Android™, iOS™, Windows™, Symbian™, Tizen™, or Bada™. At least part of the program 140, for example, may be pre-loaded on the electronic device 101 during manufacture, or may be downloaded from or updated by an external electronic device (e.g., the electronic device 102 or 104, or the server 108) during use by a user.

The OS 142 may control management (e.g., allocating or deallocation) of one or more system resources (e.g., process, memory, or power source) of the electronic device 101. The OS 142, additionally or alternatively, may include one or more driver programs to drive other hardware devices of the electronic device 101, for example, the input device 150, the sound output device 155, the display device 160, the audio module 170, the sensor module 176, the interface 177, the haptic module 179, the camera module 180, the power management module 188, the battery 189, the communication module 190, the subscriber identification module 196, or the antenna module 197.

The middleware 144 may provide various functions to the application 146 such that a function or information provided from one or more resources of the electronic device 101 may be used by the application 146. The middleware 144 may include, for example, an application manager 301, a window manager 303, a multimedia manager 305, a resource manager 307, a power manager 309, a database manager 311, a package manager 313, a connectivity manager 315, a notification manager 317, a location manager 319, a graphic manager 321, a security manager 323, a telephony manager 325, or a voice recognition manager 327.

The application manager 301, for example, may manage the life cycle of the application 146. The window manager 303, for example, may manage one or more graphical user interface (GUI) resources that are used on a screen. The multimedia manager 305, for example, may identify one or more formats to be used to play media files, and may encode or decode a corresponding one of the media files using a codec appropriate for a corresponding format selected from the one or more formats. The resource manager 307, for example, may manage the source code of the application 146 or a memory space of the memory 130. The power manager 309, for example, may manage the capacity, temperature, or power of the battery 189, and determine or provide related information to be used for the operation of the electronic device 101 based at least in part on corresponding information of the capacity, temperature, or power of the battery 189. According to an embodiment, the power manager 309 may interwork with a basic input/output system (BIOS) (not shown) of the electronic device 101.

The database manager 311, for example, may generate, search, or change a database to be used by the application 146. The package manager 313, for example, may manage installation or update of an application that is distributed in the form of a package file. The connectivity manager 315, for example, may manage a wireless connection or a direct connection between the electronic device 101 and the external electronic device. The notification manager 317, for example, may provide a function to notify a user of an occurrence of a specified event (e.g., an incoming call, message, or alert). The location manager 319, for example, may manage locational information on the electronic device 101. The graphic manager 321, for example, may manage one or more graphic effects to be offered to a user or a user interface related to the one or more graphic effects.

The security manager 323, for example, may provide system security or user authentication. The telephony manager 325, for example, may manage a voice call function or a video call function provided by the electronic device 101. The voice recognition manager 327, for example, may transmit a user's voice data to the server 108, and receive, from the server 108, a command corresponding to a function to be executed on the electronic device 101 based at least in part on the voice data, or text data converted based at least in part on the voice data. According to an embodiment, the middleware 344 may dynamically delete some existing components or add new components. According to an embodiment, at least part of the middleware 144 may be included as part of the OS 142 or may be implemented as another software separate from the OS 142.

The application 146 may include, for example, a home 351, dialer 353, short message service (SMS)/multimedia messaging service (MMS) 355, instant message (IM) 357, browser 359, camera 361, alarm 363, contact 365, voice recognition 367, email 369, calendar 371, media player 373, album 375, watch 377, health 379 (e.g., for measuring the degree of workout or biometric information, such as blood sugar), or environmental information 381 (e.g., for measuring air pressure, humidity, or temperature information) application. According to an embodiment, the application 146 may further include an information exchanging application (not shown) that is capable of supporting information exchange between the electronic device 101 and the external electronic device. The information exchange application, for example, may include a notification relay application adapted to transfer designated information (e.g., a call, message, or alert) to the external electronic device or a device management application adapted to manage the external electronic device. The notification relay application may transfer notification information corresponding to an occurrence of a specified event (e.g., receipt of an email) at another application (e.g., the email application 369) of the electronic device 101 to the external electronic device. Additionally or alternatively, the notification relay application may receive notification information from the external electronic device and provide the notification information to a user of the electronic device 101.

The device management application may control the power (e.g., turn-on or turn-off) or the function (e.g., adjustment of brightness, resolution, or focus) of the external electronic device or some component thereof (e.g., a display device or a camera module of the external electronic device). The device management application, additionally or alternatively, may support installation, delete, or update of an application running on the external electronic device.

The electronic device according to various embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that various embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

Figure 4A:
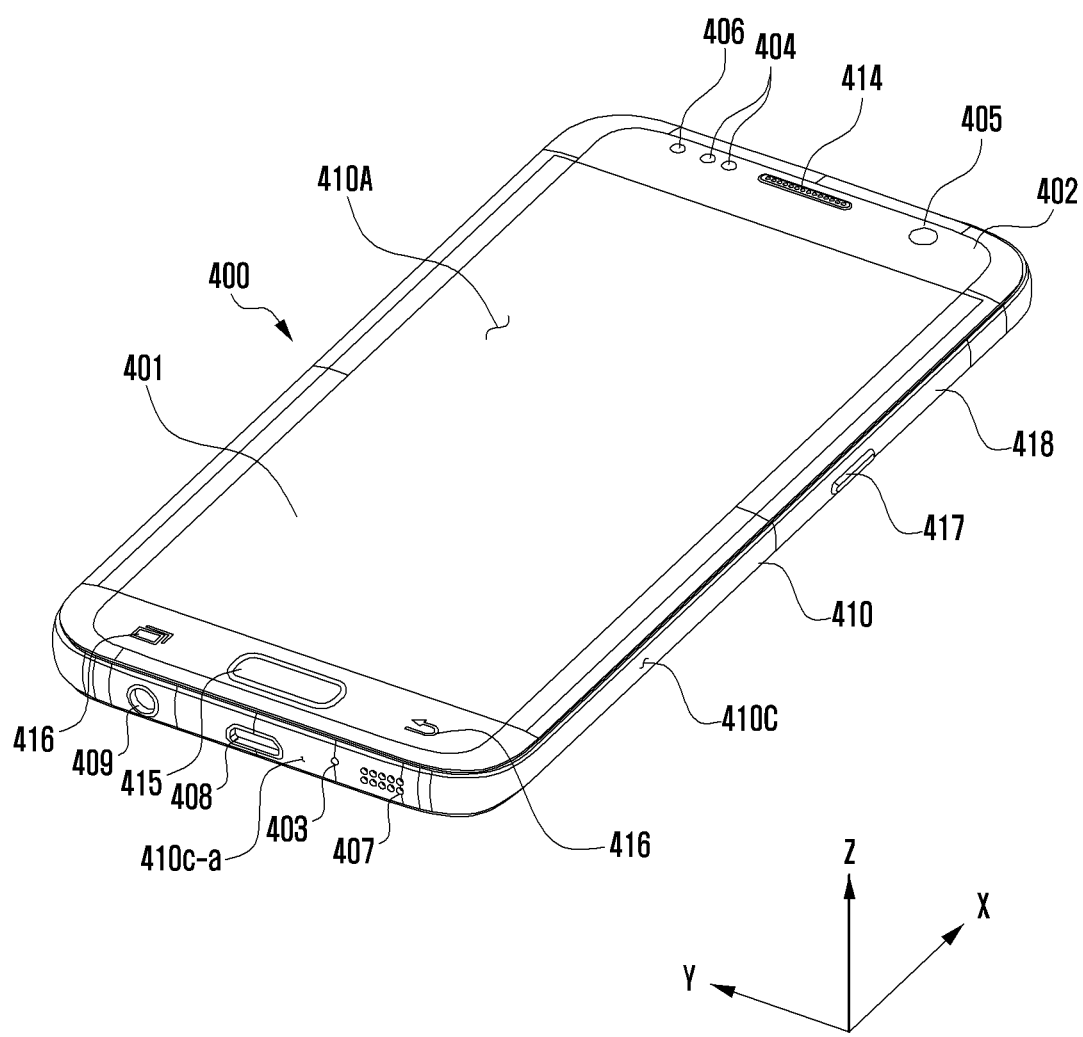
FIG. 4A is a perspective view of the front of a mobile electronic device according to an embodiment.
Figure 4B:
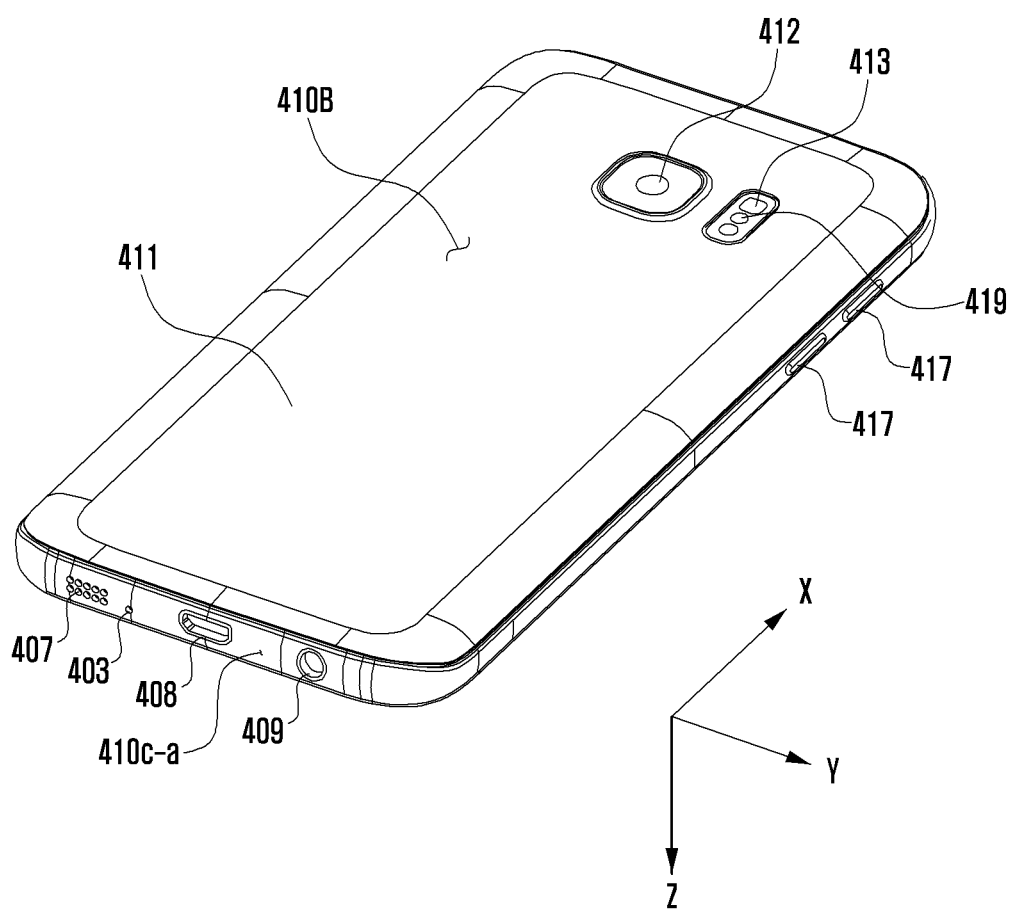
FIG. 4B is a perspective view of the rear of the electronic device shown in FIG. 4A.

FIG. 4A is a perspective view of the front of a mobile electronic device according to an embodiment, and FIG. 4B is a perspective view of the rear of the electronic device shown in FIG. 4A.

Referring to FIGS. 4A and 4B, an electronic device 400 (e.g., the electronic device 101 in FIG. 1) according to an embodiment may include a housing 410 that includes a first (or front) surface 410A, a second (or rear) surface 410B, and a side surface 410C surrounding the space between the first surface 410A and the second surface 410B. In another embodiment (not shown), the housing may refer to a structure that forms a portion of the first surface 410A, the second surface 410B, and the side surface 410C in FIG. 4. According to an embodiment, the first surface 410A may be formed as a front plate 402 of which at least a portion is substantially transparent (e.g., a glass plate or a polymer plate including various coating layers). The second surface 410B may be formed as a rear plate 411 that is substantially opaque. The rear plate 411 may be formed of, for example, coated or colored glass, ceramic, polymer, metal (e.g., aluminum, stainless steel (STS), or magnesium), or a combination of at least two thereof. The side surface 410C may be formed as a side bezel structure (or a "side member") 418 that is connected to the front plate 402 and the rear plate 411 and includes metal and/or polymer. In a certain embodiment, the rear plate 411 and the side bezel structure 418 may be integrally formed with each other, and may include the same material (e.g., a metal material such as aluminum).

According to an embodiment, the electronic device 400 may include one or more of a display 401, audio modules 403, 407, and 414, sensor modules 404 and 419, camera modules 405, 412, and 413, key input devices 415, 416, and 417, an indicator 406, and connector holes 408, and 409. In a certain embodiment, the electronic device 400 may omit at least one of the elements (e.g., key input devices 415, 416, and 417, or an indicator 406), or may further include other elements.

The display 401 may be exposed, for example, through most part of the front plate 402. The display 401 may be connected to a touch detection circuit, a pressure sensor capable of measuring the intensity (pressure) of touch, and/or a digitizer for detecting a magnetic field type stylus pen, or may be disposed adjacent thereto.

The audio modules 403, 407, and 414 may include a microphone hole 403 and speaker holes 407 and 414. Four microphones may be disposed inside the housing 410 (i.e., the space between the first surface 410A and the second surface 410B), thereby acquiring external sound through the microphone hole 403. In a certain embodiment, a plurality of microphones may be disposed inside the housing 410 to detect the direction of sound. For example, a first microphone may acquire external sound through a first microphone hole 403 formed on the lower side surface 410C_a in FIG. 4B. A second microphone may acquire external sound through a second microphone hole (not shown) formed on the upper side surface. The speaker holes 407 and 414 may include an external speaker hole 407 and a call receiver hole 414. In a certain embodiment, the speaker holes 407 and 414 and the microphone hole 403 may be implemented as one hole, or a speaker may be provided without the speaker holes 407 and 414 (e.g., piezo speakers).

The sensor modules 404 and 419 may generate electrical signals or data values corresponding to the internal operation states of the electronic device 400 or the external environment states. The sensor modules 404 and 419 may include, for example, a third sensor module 404 (e.g., a proximity sensor) and/or a second sensor module (e.g., a fingerprint sensor) (not shown), which are disposed on the first surface 410A of the housing 410, and/or a third sensor module 419 (e.g., an HRM sensor) disposed on the second surface 410B of the housing 410. The fingerprint sensor may be disposed on the second surface 410B of the housing 410, as well as on the first surface 410A thereof (e.g., a home key button 415). The electronic device 400 may further include at least one of sensor modules, which are not illustrated, such as a gesture sensor, a gyro sensor, an atmospheric pressure sensor, a magnetic sensor, an acceleration sensor, a grip sensor, a color sensor, an infrared (IR) sensor, a biometric sensor, a temperature sensor, a humidity sensor, a gas sensor (e.g., an electronic nose sensor), or an illuminance sensor. According to an embodiment, a gas sensor may be disposed inside the housing 410, and may detect components of outside air through the holes formed in the housing 410 (e.g., the first microphone holes 403 and 421, the speaker holes 407 and 414, or the connector holes 408 and 409).

The camera modules 405, 412, and 413 may include a first camera device 405 disposed on the first surface 410A of the electronic device 400, a second camera device 412, and/or a flash 413, which are disposed on the second surface 410B thereof. The camera modules 405 and 412 may include one or more lenses, image sensors, and/or image signal processors. The flash 413 may include, for example, a light-emitting diode or a xenon lamp. In a certain embodiment, two or more lenses (wide-angle and telephoto lenses) and image sensors may be disposed on one surface of the electronic device 400.

The key input devices 415, 416, and 417 may include a home key button 415 disposed on the first surface 410A of the housing 410, a touch pad 416 disposed around the home key button 415, and/or a side key button 417 disposed on the side surface 410C of the housing 410. In another embodiment, the electronic device 400 may exclude some or all of the key input devices 415, 416, and 417 mentioned above, and the excluded key input devices 415, 416, and 417 may be implemented in other forms, such as soft keys on the display 401.

The indicator 406 may be disposed, for example, on the first surface 410A of the housing 410. The indicator 406 may provide, for example, state information of the electronic device 400 in the form of light, and may include an LED.

The connector holes 408 and 409 may include a fourth connector hole 408 configured to receive a connector (e.g., a USB connector) for transmitting and receiving power and/or data to and from an external electronic device and/or a second connector hole 409 (e.g., an earphone jack) configured to receive a connector for transmitting and receiving audio signals to and from an external electronic device.

Figure 5:
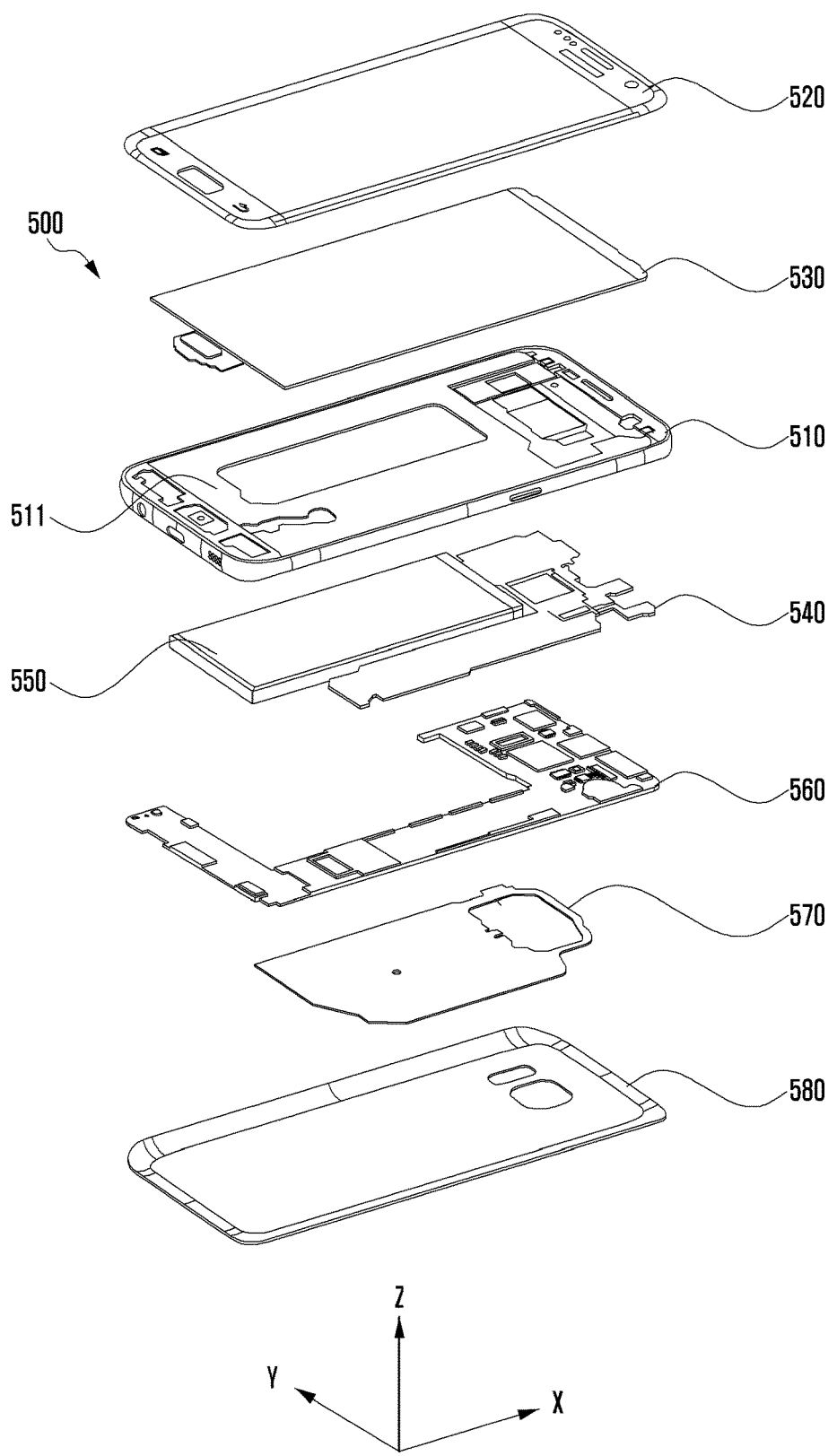
FIG. 5 is an exploded perspective view of a mobile electronic device according to an embodiment.

FIG. 5 is an exploded perspective view of a mobile electronic device according to an embodiment. Referring to FIG. 5, an electronic device 500 (e.g., the electronic device 101 in FIG. 1 or the electronic device 300 in FIG. 3) may include a side bezel structure 510, a first support member 511 (e.g., a bracket), a front plate 520, a display 530, a printed circuit board 540, a battery 550, a second support member 560 (e.g., a rear case), an antenna 570, and a rear plate 580. In a certain embodiment, an electronic device 500 may omit at least one of the elements (e.g., the first support member 511 or the second support member 560), or may further include other elements. At least one of the elements of the electronic device 500 may be the same as or similar to at least one of the elements of the electronic device 400 described with reference to FIG. 4A or 4B, and duplicate description thereof will be omitted herein.

The side bezel structure 510 may constitute a side surface (e.g., the side surface 310C in FIG. 3) of the electronic device 500. The side bezel structure 510 may have one or more holes formed therein, and electronic components (e.g., a receiver, a speaker, a microphone, a sensor, a camera, or a connector) may be mounted thereto. The electronic components may be connected to the outside through the holes. Herein, "connecting" may mean visual exposure to the outside, contact with outside air, or an electrical (or physical) connection with an external electronic device.

The first support member 511 may be disposed inside the electronic device 500, and may be connected or integrally formed with the side bezel structure 510. The first support member 511 may be formed of, for example, a metal material and/or a non-metal material (e.g., polymer). The first support member 511 may have the display 530 coupled to one surface thereof and the printed circuit board 540 coupled to the opposite surface thereof. A processor, a memory, and/or an interface may be mounted on the printed circuit board 540. The processor may include, for example, one or more of a central processing unit, an application processor, a graphic processing unit, an image signal processor, a sensor hub processor, or a communication processor.

The memory may include, for example, a volatile memory or a nonvolatile memory.

The interface may include, for example, a high definition multimedia interface (HDMI), a universal serial bus (USB) interface, an SD card interface, and/or an audio interface. The interface, for example, may electrically or physically connect the electronic device 500 to an external electronic device, and may include a USB connector, an SD card/MMC connector, or an audio connector.

The battery 550 is a device for supplying power to at least one of the elements of the electronic device 500, and may include, for example, a non-rechargeable tertiary cell, a rechargeable secondary cell, or a fuel cell. For example, at least a portion of the battery 550 and the printed circuit board 540 may be disposed on substantially the same plane. The battery 550 may be disposed inside the electronic device 300 so as to be integral therewith, or may be disposed to be detachable therefrom.

The antenna 570 may be interposed between the rear plate 580 and the battery 550. The antenna 570 may include, for example, a near-field communication (NFC) antenna, a wireless charging antenna, and/or a magnetic secure transmission (MST) antenna. The antenna 570, for example, may perform short-range communication with an external device, or may transmit and receive wireless power required for charging. In another embodiment, the antenna structure may be formed by a portion of the side bezel structure 510 and/or the first support member 511, or a combination thereof.

Figure 6A:
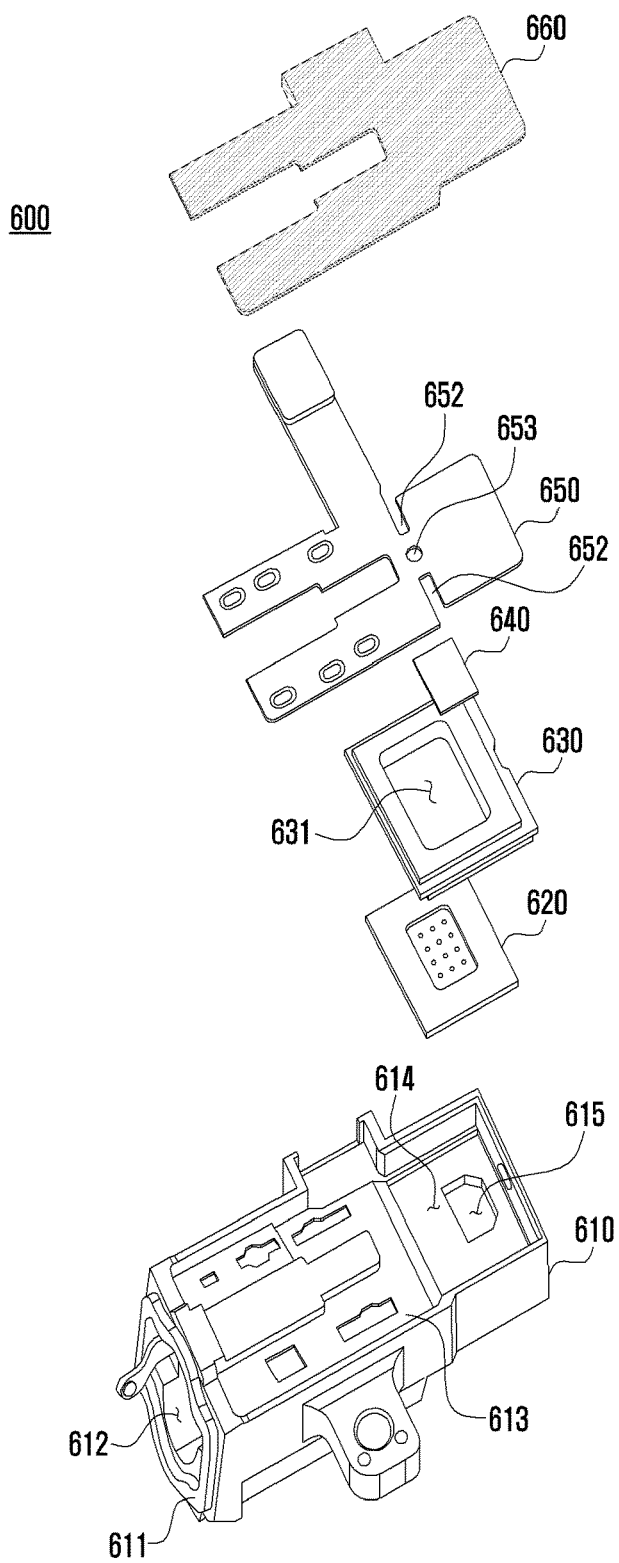
FIG. 6A is an exploded perspective view showing an earphone jack integrally formed with a gas sensor according to various embodiments.
Figure 6B:
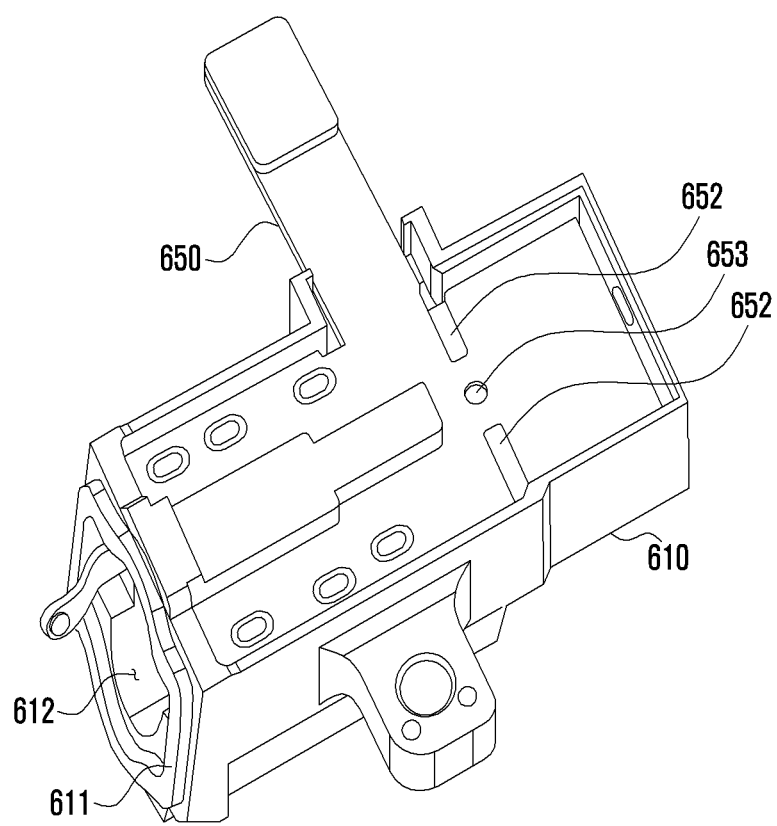
FIG. 6B is a perspective view showing an earphone jack before being sealed.
Figure 6C:
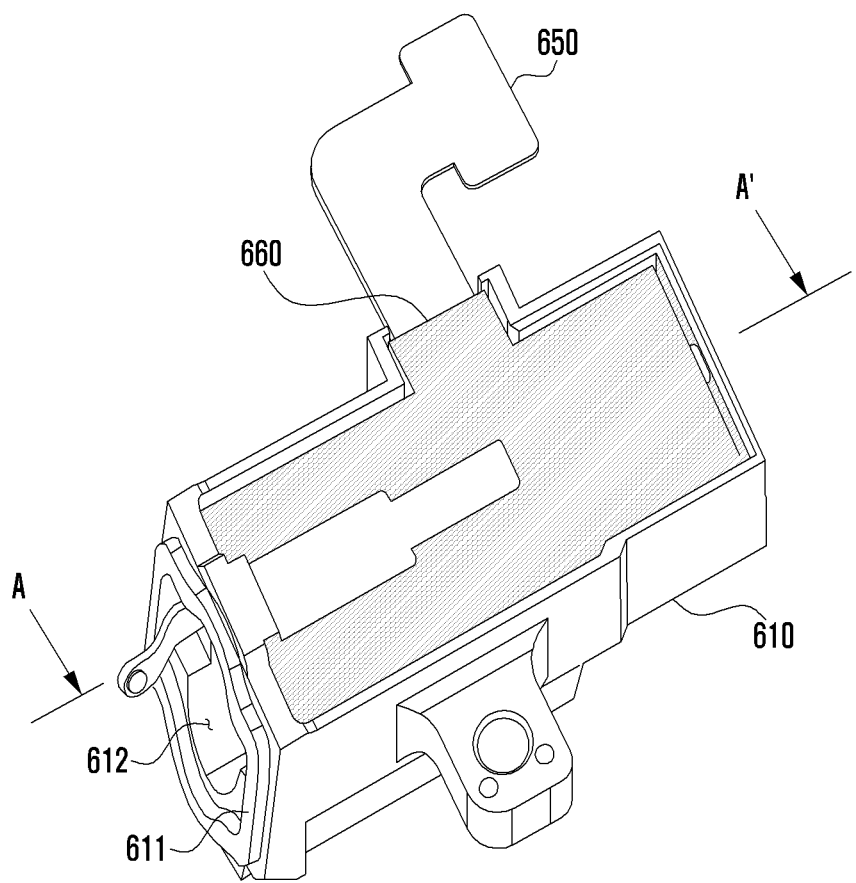
FIG. 6C is a perspective view showing an earphone jack in a sealed state.
Figure 6D:
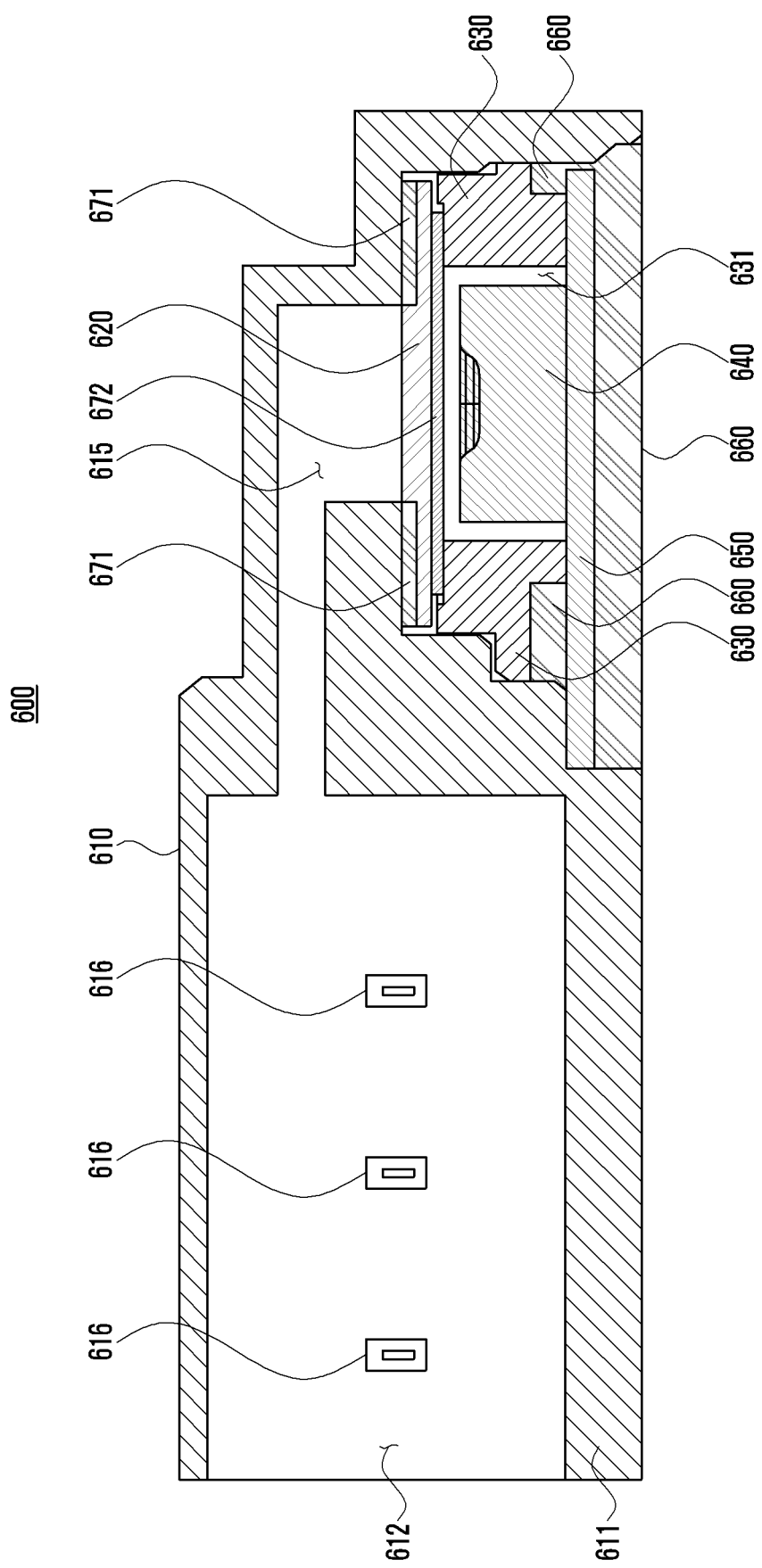
FIG. 6D is a cross-sectional view of the earphone jack taken along the line A-A' in FIG. 6C.
Figure 6E:
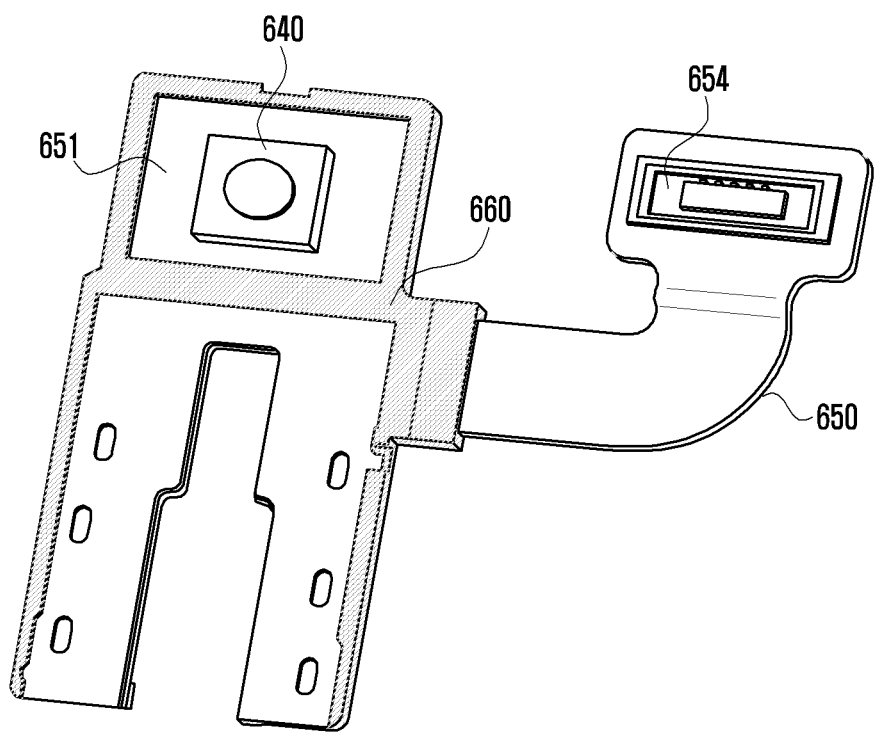
FIG. 6E is a perspective view showing the FPCB of the earphone jack in an inverted state in FIG. 6C.

FIG. 6A is an exploded perspective view showing an earphone jack integrally formed with a gas sensor according to various embodiments. FIGS. 6B and 6C are a perspective view showing an earphone jack before and after being sealed, respectively. FIG. 6D is a cross-sectional view of the earphone jack taken along the line A-A' in FIG. 6C. FIG. 6E is a perspective view showing the FPCB of the earphone jack in an inverted state in FIG. 6C.

Referring to FIG. 6A to FIG. 6E, an earphone jack 600 (e.g., the connector hole 408 in FIG. 4) according to various embodiments may include a body 610, a vent 620, a frame 630, a gas sensor 640, an FPCB 650, and a sealing member 660.

According to various embodiments, the body 610 may be positioned inside the housing so as to receive an earphone plug through an opening (e.g., the connector hole 409 in FIG. 4) formed in the housing of the electronic device.

According to various embodiments, the body 610 may have a first hole 612 formed on the side surface 611 thereof so as to receive an earphone plug. In addition, a second hole 614 to be integrated with the gas sensor 640 may be formed on the front surface 613 of the body 610. A passage 615 may be formed between the first hole 612 and the second hole 614. In other words, the passage 615 may extend from the first hole 612 to the bottom surface of the second hole 614, so that the outside air may be introduced into the second hole 614 through the first hole 612.

According to various embodiments, one surface of the vent 620 may be attached to the bottom surface of the second hole 614 using a first adhesive member 671, thereby blocking the passage 615. Accordingly, outside air may be introduced into the second hole 614 through the vent 620, whereas water is prevented from flowing thereinto.

According to various embodiments, the frame 630 may be used as a structure for positioning the gas sensor 640 in the second hole 614. For example, both the front and rear surfaces of the frame 630 are open, and the front surface may be attached to the opposite surface of the vent 620 by a second adhesive member 672. The gas sensor 640 may be inserted into the internal space 631 of the frame 630 through the open rear surface of the frame 630 while being mounted on one surface 651 of the FPCB 650. The internal space 631 of the frame in which the gas sensor 640 is disposed may be minimized in order to speed up the reaction rate and recovery rate of the gas sensor 640 for outside air. As described above, in the case where the minimization of the internal space 631 is of the priority consideration, the gas sensor 640 may be inserted into the second hole 614 without the frame 630 while being mounted on the one surface 651 of the FPCB 650.

According to various embodiments, the frame 630 may be made of a material configured to avoid outgassing into the internal space 631 inside the housing of the electronic device through the frame 630. For example, gases may be generated from various electronic components positioned inside the housing of the electronic device, and if the frame 630 is made of a material that allows the gases to pass therethrough, the accuracy of the measurement may be unreliable. Accordingly, metal or polycarbonate (PC) may be used as a material for the frame 630 in order to block the introduction of the internal gases.

According to various embodiments, the first adhesive member 671 and the second adhesive member 672 may be implemented, for example, as double-sided tapes so as to attach the vent 620 to the bottom surface of the second hole 614 and attach the frame 630 to the vent 620, respectively, while preventing outgassing from the inside of the housing of the electronic device to the gas sensor 640.

According to various embodiments, the sealing member 660 is a structure for sealing the gas sensor 640 against the inside of the housing of the electronic device, and may be disposed on the front surface of the body 610. For example, the sealing member 660 may be implemented using a plastic material (e.g., PA9T, PC, JE-851MG, etc.) and may cover the front surface of the body 610, thereby preventing the gases generated from various electronic components positioned inside the housing of the electronic device from flowing into the gas sensor 640. In addition, the sealing member 660 may be used as the structure for preventing external water from flowing into the gas sensor 640 and then into the inside of the housing of the electronic device through the terminals 616 formed on the wall of the first hole 612, which are intended to come into contact with the terminals of the earphone plug.

According to various embodiments, the sealing member 660 may be obtained by coating a paste epoxy on the front surface of the body 610 and curing the same at a high temperature.

According to various embodiments, the FPCB 650 may be designed as the structure for sealing the gas sensor 640 against the water flowing into the first hole 612. For example, as shown in the drawing, the FPCB 650 may have openings 652 formed in the form of a sandglass and a hole 653 between the openings. A portion of the epoxy applied to the front surface of the body 610 may flow into the second hole 614, in which the gas sensor 640 is positioned, through the openings 652 and the hole 653, and may then stay at the second hole 614, thereby sealing the gas sensor 640 against external water as shown in FIG. 6C.

According to various embodiments, the terminals 616 formed in the first hole 612 and the gas sensor 640 may be electrically connected to the electronic components {e.g., the processor (e.g., 120 in FIG. 1) and the audio module (e.g., 170 in FIG. 1)} mounted on the main board (e.g., 540 in FIG. 5). For example, the FPCB 650 may have a connector 654 formed thereon so as to be electrically connected to the main board of the electronic device as shown in FIG. 6E. The terminals 616 and the gas sensor 640 may be electrically connected to the main board through the connector 654.

Figure 7:
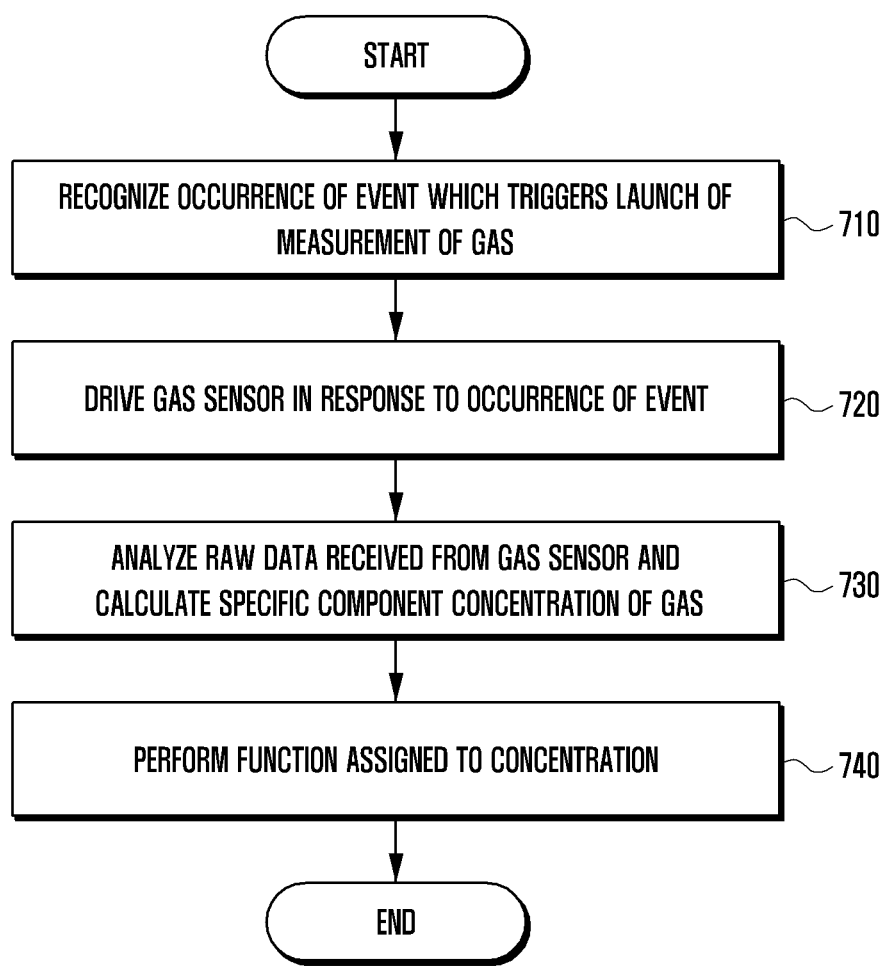
FIG. 7 is a flowchart illustrating operations of an electronic device having a gas sensor according to various embodiments.

FIG. 7 is a flowchart illustrating operations of an electronic device having a gas sensor according to various embodiments.

Referring to FIG. 7, the following operations according to various embodiments may be executed by a processor (e.g., the processor 120 in FIG. 1) of the electronic device having an earphone jack integrally formed with a gas sensor as shown in FIG. 6.

According to various embodiments, the processor may recognize the occurrence of an event that triggers the launch of measurement of gas in operation 710.

In an embodiment, the event may be a specified time (e.g., 1:00 pm). In other words, the arrival of a specified time may be recognized as the occurrence of the event.

In another embodiment, the event may be a specified place (e.g., home). For example, if the processor obtains location information of the electronic device through a wireless communication module (e.g., 192 in FIG. 1), and if the obtained location information corresponds to a specified place, the processor may recognize the arrival of the specified place as the occurrence of the event.

In another embodiment, the event may be a user input for triggering measurement of gas. For example, the user input may be a user's selection for a measurement start button displayed on the display. In addition, the user input may be a voice for requesting measurement of gas, which is received through a microphone.

In another embodiment, the event may be a call request signal to be received from or transmitted to the outside through a wireless communication module (e.g., 192 in FIG. 1). That is, the processor may recognize the reception or transmission of a call request signal as the occurrence of the event. For example, in the electronic device having an earphone jack (e.g., the earphone jack in FIG. 6) integrally formed with a gas sensor (e.g., the electronic device shown in FIG. 4, which has the microphone hole and the earphone hole formed on the same side surface), the processor may recognize a call request signal as an event for initiating the measurement of a user's health condition (e.g., an alcohol concentration in the blood or bad breath).

In another embodiment, the user's response to the reception of the call request signal may be recognized as the occurrence of the event for initiating the measurement of a user's health condition. For example, in response to the reception of the call request signal, the processor may output a sound through a speaker, a window (or a message) through a display, and/or a vibration through a haptic module. A user input indicating the acceptance of a call in response to the audible, visual, and/or tactile notification may be recognized as the event. Here, the user input may be received through an input device (e.g., a touch responsive display) or, as a user voice, through a microphone.

In another embodiment, a user input for triggering the transmission of a call request signal may be recognized as the event for initiating the measurement of a user's health condition. For example, the user input may be a user's selection for a call button displayed on the display. In addition, the user input may be a voice for requesting a call connection, which is received through a microphone.

According to various embodiments, the processor may drive the gas sensor in response to the occurrence of the event in operation 720. For example, the processor may control the gas sensor so as to obtain data related to a specific component of the outside air. As a result, the gas sensor may transfer the obtained raw data to the processor (e.g., a sensor hub processor).

According to various embodiments, the processor may further drive a temperature/humidity sensor in response to the occurrence of the event. Thus, the temperature/humidity sensor may generate raw data corresponding to the temperature/humidity, and may transmit the same to the processor.

According to various embodiments, in operation 730, the processor (e.g., a sensor hub processor) may analyze the raw data received from the gas sensor, thereby calculating the concentration {e.g., ppm (parts per million), mg/m$^3$, or μg/m$^3$} of a specific component {e.g., alcohol, volatile organic compounds (VOC), total VOC (TVOC), fine dust, carbon dioxide, bad breath (bad smell from the mouth) or the like}.

According to various embodiments, the processor may analyze the raw data received from the temperature/humidity sensor, thereby calculating the temperature/humidity, and may correct the calculated concentration, based on the calculated temperature/humidity.

According to various embodiments, in operation 740, the processor may perform a function assigned to the calculated (or corrected) concentration.

According to an embodiment, operation 740 may include an operation of providing the user with the cleanliness level (quality) of outside air. The cleanliness level of outside air, for example, may be categorized into five levels (very good, good, moderate, bad, and very bad), and the processor may output a message indicating the level corresponding to the calculated (or corrected) concentration through a display and/or a speaker.

According to an embodiment, operation 740 may include an operation of providing the user with an alcohol concentration in the blood or the degree of bad breath. For example, if the alcohol concentration in the blood exceeds a predetermined value (for example, the value corresponding to suspension of a driver's license), the processor may output a warning message through a display and/or a speaker.

According to an embodiment, operation 740 may include an operation of controlling ON/OFF and a function of an external electronic device {e.g., an IoT (internet of things) device} connected to the electronic device through the wireless communication module, bases on the calculated (or corrected) concentration. For example, if the alcohol concentration in the blood exceeds a predetermined value (e.g., the value corresponding to suspension of a driver's license), the processor may transmit an operation stop command to an electronic control system of a vehicle. As another example, based on the air cleanliness level (for example, if the air cleanliness level corresponds to a bad level), the processor may control an air cleaner, an air conditioner, a heater, a humidifier, a dehumidifier, or the like, thereby enhancing the cleanliness level.

According to an embodiment, operation 740 may include an operation of adjusting a measurement period of the gas sensor, based on the calculated (or corrected) concentration. For example, as shown in Table 1, as the cleanliness level becomes higher, the processor may increase the measurement period, thereby reducing the current consumption.

TABLE 1

| Concentration of TVOC | Cleanliness level of air | Measurement period |
| --- | --- | --- |
| Level 1 (TVOC < 0.3 mg/m$^3$) | Very good | Once every 30 seconds |
| Level 2 (TVOC > 0.3 mg/m$^3$) | Good | Once every 20 seconds |
| Level 3 (TVOC > 3 mg/m$^3$) | Moderate | Once every 10 seconds |
| Level 4 (TVOC > 10 mg/m$^3$) | Bad | Once every 5 seconds |
| Level 5 (TVOC > 25 mg/m$^3$) | Very bad | Once every 3 seconds |

Figure 8:
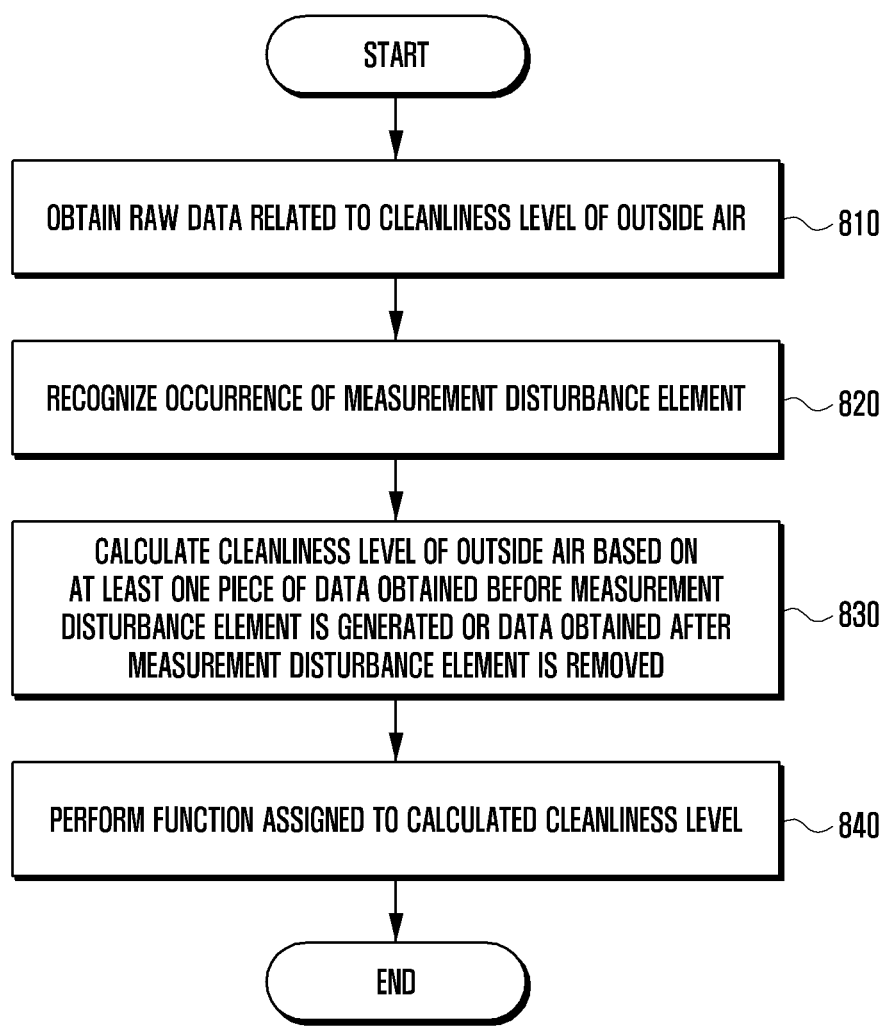
FIG. 8 is a flowchart illustrating operations of an electronic device having a gas sensor according to various embodiments.

According to an embodiment, operation 740 may include an operation of providing the outside (e.g., a user and/or an external electronic device) with concentration, a change thereof, or information corresponding thereto. For example, if the cleanliness level of air is changed, an alarm message may be output through a display and/or a speaker. If the cleanliness level of air changes abruptly (for example, referring to Table 1, the cleanliness level of air changes to level 5 within minutes), the processor may output a message (e.g., fire alarm) corresponding to the change through a display and/or a speaker. In addition, the processor may transmit the message corresponding to the change to a fire station. FIG. 8 is a flowchart illustrating operations of an electronic device having a gas sensor according to various embodiments.

Referring to FIG. 8, the following operations according to various embodiments may be executed by the processor (e.g., the processor 120 in FIG. 1) of the electronic device having the earphone jack integrally formed with the gas sensor as shown in FIG. 6.

The raw data collected during a proximity call (i.e., the call performed while the user places his/her ear close to the receiver) may lead to inaccuracy in calculation of the cleanliness level. For example, during the proximity call, the air from the user's mouth may be mixed with the outside air to then flow into the earphone hole (e.g., 403 in FIG. 4), which may cause inaccurate calculation of the cleanliness level of the outside air. As another example, the earphone plug inserted into the earphone jack (e.g., the earphone jack 600 in FIG. 6) may hinder the outside air from flowing into the first hole 612, so that the calculation of the cleanliness level may be inaccurate.

According to various embodiments of the disclosure, the processor may perform an operation of measuring gas (e.g., operations below) in consideration of measurement disturbance elements such as the proximity call or the insertion of a plug as described above.

According to various embodiments, in operation 810, the processor may control the gas sensor so as to obtain raw data related to the cleanliness level of the outside air.

According to various embodiments, in operation 820, the processor may recognize the occurrence of a measurement disturbance element while the gas sensor is obtaining the raw data.

According to an embodiment, the processor may recognize an operation of a user's proximity call, based at least on the data obtained from a proximity sensor. For example, if the data value obtained from the proximity sensor indicates the operation in which the user places an electronic device close to his/her face (e.g., cheek), or if the obtained data value is less than a threshold value representing a specific distance in a specific state {for example, after receiving a call request signal from the outside through a wireless communication module (e.g., 192 in FIG. 1), after transmitting a call request signal to the outside through a wireless communication module, or during a call with an external device through a wireless communication module}, the processor may recognize that the operation of initiating a user's proximity call (measurement disturbance element) has occurred. In addition, if a data value obtained from the proximity sensor indicates an operation in which the user moves the electronic device away from him/her, or if the obtained data value exceeds the threshold value after recognizing the operation of initiating the proximity call, the processor may recognize that an operation for terminating the user's proximity call has occurred (that is, the measurement disturbance element has been removed).

According to an embodiment, the processor may detect the insertion or release of the earphone plug through the audio module (e.g., 170 in FIG. 1), and may recognize the insertion of the earphone plug as the occurrence of the measurement disturbance element and the release of the earphone plug as the removal of the measurement disturbance element. For example, the terminal formed in the hole of the earphone jack (e.g., the first hole 612 in FIG. 6) comes into contact with the earphone plug, thereby generating an electrical signal (or a change thereof) (hereinafter, referred to as an "earphone detection signal"). The earphone detection signal may be transmitted to the audio module (e.g., 170 in FIG. 1). The audio module (e.g., 210 in FIG. 2) may transmit, to the processor (e.g., a sensor hub processor), the earphone detection signal along with information indicating the time of detecting the same (e.g., a time frame). The processor may recognize the occurrence of a measurement disturbance element by the reception of the earphone detection signal. Meanwhile, if the earphone plug is separated from the earphone jack, an electrical signal (or a change thereof) (hereinafter, referred to as an "earphone separation signal") may be generated according thereto. The earphone separation signal may be transmitted to the processor through the audio module along with information indicating the time of separating the same.

According to various embodiments, in operation 830, the processor may calculate the cleanliness level of the outside air, based on at least one piece of the raw data obtained before the occurrence of the measurement disturbance element (e.g., the initiation of the proximity call or the insertion of the earphone plug) or the raw data obtained after the removal of the measurement disturbance element. For example, the processor may obtain an average value of the raw data collected for a determined period of time, and may calculate the cleanliness level using the average value. In this case, in calculating the average value, the raw data collected while the measurement disturbance element is sustained may be excluded. Alternatively, the processor may stop the collection of the raw data (e.g., storing the raw data in memory) while the measurement disturbance element is sustained, and may resume the collection operation if the measurement disturbance element is removed.

According to a certain embodiment, the raw data collected while the measurement disturbance element is sustained may not be discarded, and may be used in measuring the user's health condition. Additionally, the processor may correct the obtained cleanliness level, based on the temperature/humidity obtained through the temperature/humidity sensor.

According to various embodiments, in operation 840, the processor may perform a function assigned to the calculated (or corrected) cleanliness level. For example, operation 840 may include an operation of providing the user with the cleanliness level of the outside air, an operation of controlling ON/OFF and functions of an external electronic device {e.g., an IoT (internet of things) device}, based on the cleanliness level, an operation of adjusting the measurement cycle of the gas sensor, based on the cleanliness level, or an operation of providing the outside (e.g., the user and/or the external electronic device) with a change in cleanliness level or information corresponding thereto.

Figure 9:
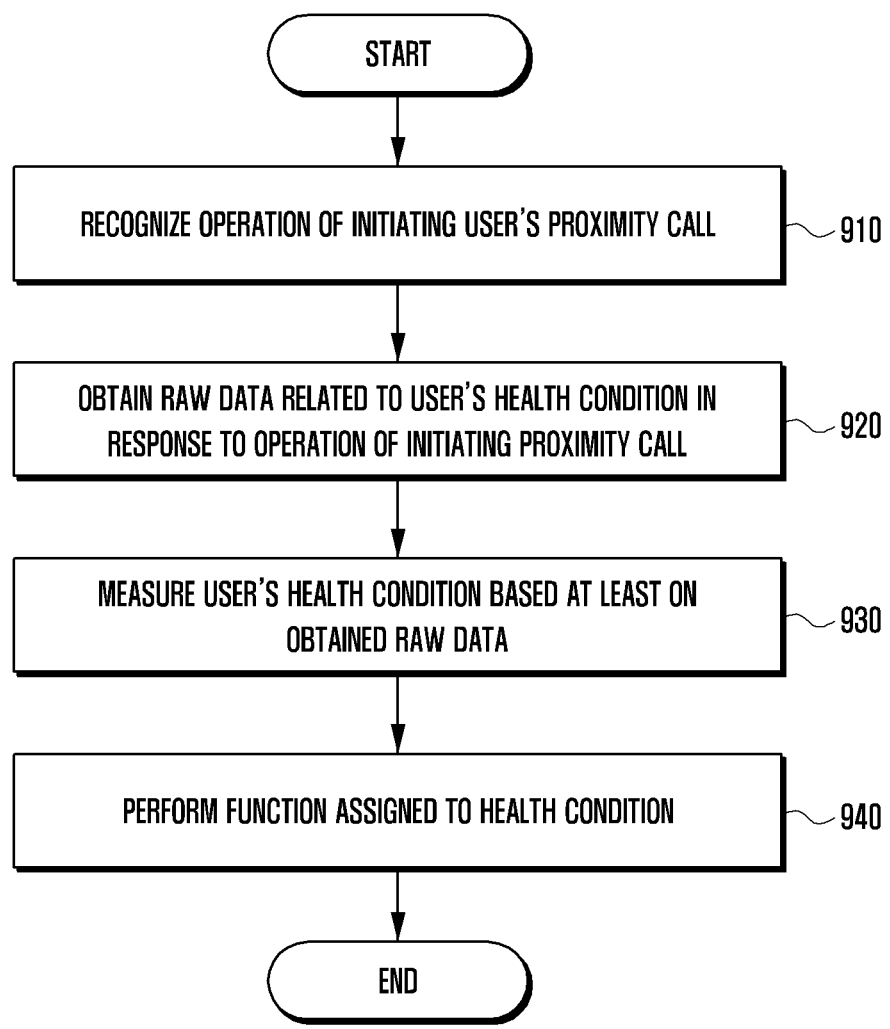
FIG. 9 is a flowchart illustrating operations of an electronic device having a gas sensor according to various embodiments.

FIG. 9 is a flowchart illustrating operations of an electronic device having a gas sensor according to various embodiments.

Referring to FIG. 9, the following operations according to various embodiments may be executed by a processor (e.g., the processor 120 in FIG. 1) of the electronic device (e.g., the electronic device shown in FIG. 4, which has the microphone hole and the earphone hole formed on the same side surface) having an earphone jack integrally formed with a gas sensor as shown in FIG. 6.

According to various embodiments, in operation 910 the processor may recognize an operation of initiating a user's proximity call. According to an embodiment, the processor may recognize the operation of initiating a proximity call, based on the data obtained from at least one sensor (e.g., an acceleration sensor, a proximity sensor, etc.).

According to various embodiments, in operation 920 the processor may control the gas sensor so as to obtain raw data related to a user's health condition in response to the operation of initiating the user's proximity call. According to an embodiment, the raw data may continue to be obtained for a predetermined period of time after recognizing the operation of initiating the proximity call. According to another embodiment, the raw data may continue to be obtained until the termination of the proximity call is recognized.

According to various embodiments, in operation 930, the processor may measure a user's health condition (e.g., an alcohol concentration in the blood or a concentration of bad breath), based on the raw data obtained by the gas sensor after recognizing the operation of initiating the proximity call. Additionally, the processor may correct the calculated cleanliness level, based on the temperature/humidity obtained through the temperature/humidity sensor. Additionally, in measuring the health condition, it may be considered whether or not an earphone plug is inserted. For example, the processor may measure the user's health condition, based at least on the raw data obtained by the gas sensor after recognizing the operation of initiating the proximity call, in the state in which the earphone plug is separated from the earphone jack.

According to various embodiments, in operation 940, the processor may perform a function assigned to the calculated (or corrected) health condition. For example, operation 940 may include an operation of providing the user with an alcohol concentration in the blood or the degree of bad breath, an operation of controlling ON/OFF or functions of an external electronic device {e.g., an IoT (internet of things) device}, based on the health condition, an operation of adjusting the measurement cycle of the gas sensor, based on the health condition, or an operation of providing the outside (e.g., the user and/or the external electronic device) with a change in health condition or information corresponding thereto.

An electronic device according to various embodiments may include: a housing having a hole formed therethrough; an earphone jack built in the housing so as to receive an earphone plug therein through the hole; a gas sensor integrally formed with the earphone jack; a memory positioned inside the housing; and a processor positioned inside the housing and electrically connected to the earphone jack, the gas sensor, and the memory, wherein the memory may store instructions that cause, when executed, the processor to: control the gas sensor so as to obtain data related to a specific component of outside air; and calculate a cleanliness level of the outside air, based on at least one piece of data obtained by the gas sensor before a predetermined measurement disturbance element is generated or data obtained by the gas sensor after the measurement disturbance element is removed.

The instructions may cause the processor to recognize the insertion of an earphone plug into the earphone jack as the measurement disturbance element.

The electronic device may further include a proximity sensor and a wireless communication module electrically connected to the processor, wherein the instructions may cause the processor to: recognize an operation of initiating a user's proximity call, based at least on data obtained from the proximity sensor, while communicating with an external device through the wireless communication module; and recognize the operation of initiating the proximity call as the measurement disturbance element.

The earphone jack may be configured to include a first hole configured to receive the earphone plug, a second hole configured to accommodate the gas sensor, and a passage formed between the first hole and the second hole so as to allow the outside air to be introduced into the second hole through the first hole.

The electronic device may further include a vent configured to block the passage to prevent water from flowing into the second hole through the first hole.

The electronic device may further include a structure configured to seal the second hole against gas generated inside the housing.

The electronic device may further include a display and a wireless communication module electrically connected to the processor, wherein the instructions may cause the processor to output information related to the calculated cleanliness level to the outside through at least one of the display or the wireless communication module.

The electronic device may further include a wireless communication module electrically connected to the processor, wherein the instructions may cause the processor to drive the gas sensor if location information obtained through the wireless communication module corresponds to a specified place.

An electronic device according to various embodiments may include: a housing having a first hole and a second hole formed therethrough; an earphone jack built in the housing so as to receive an earphone plug therein through the first hole; a gas sensor integrally formed with the earphone jack; a microphone built in the housing so as to lead to the outside through the second hole; a proximity sensor positioned inside the housing; a wireless communication module positioned inside the housing; a memory positioned inside the housing; and a processor positioned inside the housing and electrically connected to the earphone jack, the gas sensor, the microphone, the proximity sensor, the wireless communication module, and the memory, wherein the first hole and the second hole may be formed on one side surface of the housing, and wherein the memory may store instructions that cause, when executed, the processor to: recognize an operation of initiating a user's proximity call, based at least on data obtained from the proximity sensor, while communicating with an external device through the wireless communication module; and measure a user's health condition, based at least on data obtained by the gas sensor after recognizing the operation of initiating the proximity call.

The instructions may cause the processor to measure the user's health condition, based on data obtained by the gas sensor after recognizing the operation of initiating the proximity call and before recognizing an operation of terminating the proximity call.

The electronic device may further include a display and a wireless communication module electrically connected to the processor, wherein the instructions may cause the processor to output information related to the health condition to the outside through at least one of the display or the wireless communication module.

The instructions may cause the processor to drive the gas sensor in response to the occurrence of a call-related event.

The instructions may cause the processor to drive the gas sensor if sound is obtained from the outside through the microphone.

A method for operating an electronic device may include: obtaining data related to a specific component of outside air by a gas sensor of the electronic device; recognizing the occurrence of a predetermined measurement disturbance element by a processor of the electronic device; and calculating a cleanliness level of the outside air by the processor, based on at least one piece of data obtained by the gas sensor before the measurement disturbance element is generated or data obtained by the gas sensor after the measurement disturbance element is removed, wherein the measurement disturbance element may be an operation of inserting an earphone plug into an earphone jack of the electronic device or an operation of initiating a user's proximity call.

The recognizing may include recognizing the operation of initiating the proximity call by the processor, based at least on data obtained from a proximity sensor of the electronic device.

The method may further include an operation of outputting information related to the calculated cleanliness level to the outside.

The outputting may include displaying the information on a display of the electronic device.

The outputting may include transmitting the information to an external electronic device through the wireless communication module of the electronic device.

The information may include a command for controlling the external electronic device.

The method may further include driving the gas sensor if location information obtained through the wireless communication module of the electronic device corresponds to a specified place.

The embodiments of the disclosure described and shown in the specification and the drawings have been presented to easily explain the technical contents of the embodiments of the disclosure and help understanding of the embodiments of the disclosure, and are not intended to limit the scope of the embodiments of the disclosure. Therefore, the scope of the embodiments of the disclosure shall be construed to include, in addition to the embodiments disclosed herein, all modifications and changes derived on the basis of the technical idea of various embodiments of the disclosure.

The invention claimed is:

1. An electronic device comprising:
   a housing having a first hole formed therethrough;
   an earphone jack built in the housing so as to receive an earphone plug therein through the first hole;
   a gas sensor integrally formed with the earphone jack;
   a memory positioned inside the housing; and
   a processor positioned inside the housing and electrically connected to the earphone jack, the gas sensor, and the memory, wherein the memory stores instructions that cause, when executed, the processor to:

control the gas sensor so as to obtain data related to a specific component of outside air; and calculate a cleanliness level of the outside air, based at least in part on first data obtained from the gas sensor before the earphone plug is inserted into the earphone jack, and second data is obtained from the gas sensor after the earphone plug is removed from the earphone jack, wherein the earphone jack comprises:

a second hole configured to accommodate the gas sensor;

a passage formed between the first hole and the second hole so as to allow the outside air to be introduced into the second hole through the first hole; and a vent blocking the passage to prevent water from flowing into the second hole through the first hole.

2. The electronic device of claim 1, further comprising a proximity sensor and a wireless communication module electrically connected to the processor, wherein the instructions cause the processor to:

recognize an operation of initiating a user's proximity call, based at least on data obtained from the proximity sensor, while communicating with an external device through the wireless communication module.

3. The electronic device of claim 1, further comprising a structure configured to seal the second hole against gas generated inside the housing.

4. The electronic device of claim 1, further comprising a display and a wireless communication module electrically connected to the processor, wherein the instructions cause the processor to output information related to the calculated cleanliness level to the outside through at least one of the display or the wireless communication module.

5. The electronic device of claim 1, further comprising a wireless communication module electrically connected to the processor, wherein the instructions cause the processor to drive the gas sensor if location information obtained through the wireless communication module corresponds to a specified place.

6. The electronic device of claim 1, further comprising:

a microphone built in the housing so as to lead to the outside through the second hole;

a proximity sensor positioned inside the housing; and a wireless communication module positioned inside the housing; and wherein the memory stores instructions that cause, when executed, the processor to:

recognize an operation of initiating a user's proximity call, based at least on data obtained from the proximity sensor, while communicating with an external device through the wireless communication module; and measure a user's health condition, based at least on data obtained by the gas sensor after recognizing the operation of initiating the user's proximity call.

7. The electronic device of claim 6, wherein the instructions cause the processor to measure the user's health condition, based on data obtained by the gas sensor after recognizing the operation of initiating the user's proximity call and before recognizing an operation of terminating the user's proximity call.

8. The electronic device of claim 6, further comprising a display, wherein the wireless communication module electrically connected to the processor, and wherein the instructions cause the processor to output information related to the user's health condition to the outside through at least one of the display or the wireless communication module.

9. The electronic device of claim 6, wherein the instructions cause the processor to drive the gas sensor in response to occurrence of a call-related event.

10. The electronic device of claim 6, wherein the instructions cause the processor to drive the gas sensor if sound is obtained from the outside through the microphone.

* * * * *